US005620953A

United States Patent [19]
Cannova et al.

[11] Patent Number: 5,620,953
[45] Date of Patent: Apr. 15, 1997

[54] ANTIPROTOZOAL CYCLIC TETRAPEPTIDES

[75] Inventors: Christine L. Cannova, Toms River; Michael A. Goetz, Scotch Plains; Anne W. Dombrowski, East Brunswick; Sandra J. Rattray; Sheo B. Singh, both of Edison; Gerald F. Bills, Clark; Jon Polishook, Cranford; Joyce A. Greene, Clark; Gary K. Darland, Mountainside, all of N.J.

[73] Assignee: Merck & Co., Inc., Rahway, N.J.

[21] Appl. No.: 447,664

[22] Filed: May 23, 1995

Related U.S. Application Data

[63] Continuation-in-part of Ser. No. 281,325, Jul. 27, 1994, abandoned.

[51] Int. Cl.$^6$ .............. C07K 5/12; A61K 38/12; A61K 31/445; C07D 471/04
[52] U.S. Cl. .............. 514/10; 540/460; 514/11; 514/183; 514/10; 530/321
[58] Field of Search .............. 540/460; 514/183, 514/11, 10; 530/321

[56] References Cited

U.S. PATENT DOCUMENTS

| | | | |
|---|---|---|---|
| 4,233,291 | 11/1980 | Simone-Lavoine et al. | 424/177 |
| 4,430,431 | 2/1984 | Servier | 435/171 |
| 5,049,546 | 9/1991 | Sesin et al. | 514/9 |
| 5,114,918 | 5/1992 | Ishikawa et al. | 514/11 |
| 5,300,491 | 4/1994 | Andrews et al. | 514/10 |

OTHER PUBLICATIONS

Laskin, et al, CRC Handbook of microbiology, vol. II, Funji, Algae, Protozoa, and Viruses, Pub. 1984 By CRC Press (West Palm Beach), pp. 101–108, 138, 286, 802 and 803.

Helvetica Chimica Acta–vol. 57, Fasc. 3 (1974)–Nr. 61 pp. 533–545–This article describes the isolation and structure determination of the cyclic tetrapeptide chlamydocin.

The Journal Of Antibiotics, vo. XLIII No. 12, Hiroshi Itazaki, et al pp. 1524–1532 (1990) Dec.

Tetrahedron, vol. 38, No. 1 pp. 45–48, Jerrold M. Liesch, et al (1982).

The Journal of Antibiotics, vol. XXXVI, No. 5, pp. 478–483, Kazuyoshi Umehara, et al (May 1983).

Agr. Biol. Chem., 37 (4), 955–956, Akira Hirota, et al (1973).

J. Med. Chem., 30, 71–78, Richard E. Shute, et al. (1987).

*Primary Examiner*—Mukund J. Shah
*Assistant Examiner*—King L. Wong
*Attorney, Agent, or Firm*—Mollie M. Yang; David L. Rose

[57] ABSTRACT

The present invention provides novel cyclic tetrapeptides useful in the treatment or prevention of protozoal diseases; in particular, the novel compounds are active against the causative pathogens in malaria, toxoplasmosis, and coccidiosis.

5 Claims, No Drawings

ANTIPROTOZOAL CYCLIC TETRAPEPTIDES

CROSS REFERENCE

This is a continuation-in-part of application Ser. No. 08/281,325 filed Jul. 27, 1994, now abandoned, which is hereby incorporated by reference in its entirety.

BACKGROUND OF THE INVENTION

Parasitic protozoa are responsible for a wide variety of infections in man and animals. Many of the diseases are life threatening to the host and cause considerable economic loss in animal husbandry. For example, malaria remains a significant health threat to humans despite massive international attempts to eradicate the disease; trypanosomiasis such as Chagas disease caused by *Trypanosoma cruzi* and African sleeping sickness caused by *T. brucei* are not uncommon in Africa and South America; and opportunistic infections in immunocompromised hosts caused by *Pneumocystis carinii, Toxoplasma gondii, Cryptosporidium sp.* are becoming increasingly significant in the developed countries.

A protozoal infection of great economic importance is coccidiosis, a widespread disease of domesticated animals produced by infections by protozoa of the genus Eimeria. Some of the most significant Eimeria species are those in poultry, namely *E. tenella, E. acervulina, E. necatrix, E. brunetti* and *E. maxima*. The disease is responsible for high levels of morbidity and mortality in poultry and can result in extreme economic losses.

In some protozoal diseases, such as Chagas disease, there is no satisfactory treatment; in others, drug-resistant strains of the protozoa may develop. Accordingly, there exists a continued need to identify new and effective anti-protozoal drugs.

SUMMARY OF THE INVENTION

The present invention relates to novel cyclic tetrapeptides, their use as antiprotozoal agents, pharmaceutical compositions thereof, and method for producing the cyclic tetrapeptides by fermentation of Fusarium spp.

DETAILED DESCRIPTION OF THE INVENTION

In one aspect, the present invention relates to novel cyclic tetrapeptides having the formula I:

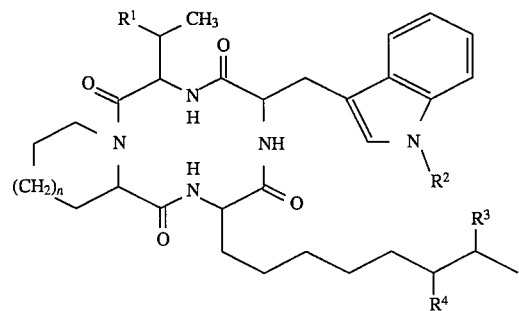

wherein
$R^1$ is $CH_3$ or $CH_2CH_3$;
$R^2$ is H or $-OCH_3$;
$R^3$ is H and $R^4$ is =O or (H, OH); or
$R^3$ is OH and $R^4$ is =O or (H, H); and n is 0 or 1;
with the proviso that when n is 0, $R^1$ is $CH_2CH_3$, $R^3$ is H and $R^4$ is =O; and that when $R^1$ is $CH_3$, $R^3$ is H and $R^4$ is =O; or a pharmaceutically acceptable salt thereof.

In the above definition, $R^4$ may represent an oxo group, a hydrogen and a hydroxy, or two hydrogen atoms.

Compounds of the present invention contain several asymmetric centers and may thus give rise to diastereomers and optical isomers. The present invention is meant to comprehend such possible diastereomers as well as their racemic and resolved, enantiomerically pure forms and pharmaceutically acceptable salts thereof.

In one embodiment, compounds of the present invention have the following stereochemical configuration (shown as formula I'):

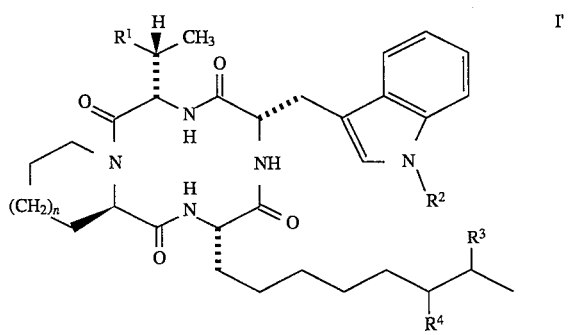

Preferred compounds of the present invention are those of formula I' wherein the substituents are as follows:

| Compound | n | $R^1$ | $R^2$ | $R^3$ | $R^4$ |
|---|---|---|---|---|---|
| Ia | 1 | Et | OMe | H | =O |
| Ib | 1 | Et | H | H | =O |
| Ic | 1 | Me | OMe | H | =O |
| Id | 0 | Et | OMe | H | =O |
| Ie | 1 | Et | OMe | H | (H,OH) |
| If | 1 | Et | OMe | OH | =O |
| Ig | 1 | Et | OMe | OH | (H,H) |
| Ih | 0 | Et | H | H | =O |

In a second aspect, the present invention provides a method for the production of a compound of formula I which comprises cultivating a strain of *Fusarium pallidoroseum* capable of producing said compound, in a nutrient medium containing assimilable sources of carbon and nitrogen, and recovering said compound. In a preferred embodiment, the strain of *Fusarium pallidoroseum* is one having the identifying characteristics of ATCC 74289.

In a third aspect, the present invention provides a method for the production of a compound of formula Ia, Ib, Ic, Ie, If or Ig which comprises cultivating a strain of *Fusarium sp.* ATCC 74322 capable of producing said compound, in a nutrient medium containing assimilable sources of carbon and nitrogen, and recovering said compound.

In a fourth aspect, the present invention provides a method for the treatment or prevention of protozoal diseases which comprises administering an antiprotozoal effective amount of a compound of formula I to a host in need of treatment or prevention.

In a fifth aspect, the present invention provides a composition useful for the treatment or prevention of protozoal diseases which comprises an inert carrier and an effective amount of a compound of formula I.

In a sixth aspect, the present invention provides a biologically pure culture of a *Fusarium pallidoroseum* having the identifying characteristics of ATCC 74289, and capable of producing a compound of formula I in a nutrient medium containing assimilable sources of carbon and nitrogen.

In seventh aspect, the present invention provides a biologically pure culture of a *Fusarium sp.* having the identifying characteristics of ATCC 74322, and capable of producing a compound of formula I in a nutrient medium containing assimilable sources of carbon and nitrogen.

Compounds of formula I are either isolated from the fermentation broth of producing organisms, or are prepared from such natural products via chemical manipulations; some compounds may be obtained by either method.

The term "pharmaceutically acceptable salts" refers to salts prepared from pharmaceutically acceptable non-toxic bases or acids. When the compound of the present invention is acidic, salts may be prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary, and tertiary amines, substituted amines including naturally occurring substituted amines, cyclic amines and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric, and tartaric acids.

DESCRIPTION OF THE PRODUCING ORGANISM

Compounds Ia to Ig are produced by the fermentation of the fungus *Fusarium pallidoroseum* (Cooke) Sacc. (MF6040) (Deuteromycotina, Hyphomycetes) isolated from branches of *Acacia sp.* collected in Santa Rosa National Park, Guanacaste Province, Costa Rica. A culture of this organism has been deposited with the American Type Culture Collection (Rockville, Md., USA) on Jul. 6, 1994 under the BUDAPEST TREATY ON THE INTERNATIONAL RECOGNITION OF THE DEPOSIT OF MICROORGANISMS FOR THE PURPOSES OF PATENT PROCEDURE and assigned the accession number ATCC 74289.

The fungus was isolated by the surface sterilization method described in Bills and Polishook, Recovery of Endophytic Fungi from *Chamaecyparis thyoides*. Sydowia, 1992, 44:1–12. In the following descriptions, capitalized color names are from Ridgway, *Color Standards and Color Nomenclature*. Publ. by the author, Washington, D.C. 43 p. +53 pl. (1912).

On cornmeal agar (Difco), colony attaining a diameter of 43 mm after 7 days at 25° C., 67% relative humidity and 12 hr fluorescent light photoperiod was observed. Colony mat was white, cottony, floccose. Aerial mycelium was 2–3 mm high. Exudate and soluble pigment were absent, and reverse was uncolored. No growth at 37° C.

On oatmeal agar (Difco), colony attaining a diameter of 50 mm after 7 days under the same conditions for cornmeal agar was observed. Colony mat was white, woolly throughout, with a zone of yellow (Naples Yellow) in the middle of colony. Aerial mycelium was 4–5 mm high throughout. Exudate and soluble pigment were absent, and reverse was uncolored. No growth at 37° C.

On potato-dextrose agar (Difco), colony attaining a diameter of 22 mm after 7 days under the same conditions for cornmeal agar was observed. Colony mat was white, woolly. Aerial mycelium was of unequal lengths 1–2 mm to 4–5 mm high giving the culture a clumpy appearance, and reverse was pale orange (Salmon Color, Salmon-Buff). Exudate and soluble pigment were absent. No growth at 37° C.

On malt-yeast extract agar (1% malt extract, 0.2% yeast extract), colony attaining a diameter of 45 mm after 7 days under the same conditions for cornmeal agar was observed. Colony mat was white, cottony to woolly, with a yellow (Picric Yellow, Pale Lemon Yellow) zone midway through colony. Aerial mycelium was 2–3 mm high throughout, margin hyaline, appressed, and reverse was pale yellow (Light Ochraceous-Buff, Warm Buff). Exudate and soluble pigment were absent. No growth at 37° C.

Aerial hyphae were thin-walled, flexuous, septate, hyaline, 3.0–4.0 μm wide. Conidiophores were hyaline, septate, scattered in aerial mycelium and prostrate mycelium, phialides cylindrical, producing 1 conidium per opening, sympodially branched, 15–24×3.0–3.2 μm. Macroconidia fusiform, nearly straight, hyaline, pedicillate basal cell, usually 3–5 septate, variable in size, 30–44×3.2–4.8 μm Microconidia, sporodochia and chlamydospores were absent. No teleomorph was observed.

The key taxonomic characteristics of this species include floccose aerial hyphae with scattered conidiophores, absence of sporodochia and microconidia, and in culture a peach colored reverse. In addition, the macroconidia are nearly straight with a slight bend at each end. These key characters agree well with published descriptions for *F. pallidoroseum*. (Nelson, et al. Fusarium species, an Illustrated Manual for Identification. The Pennsylvania University Press, University Park, Pa. 193p, 1983; and Domsch, et al., Compendium of Soil Fungi, Vol. 1., Academic Press. New York. 859 p., 1980). In the older literature, this fungus is called *Fusarium semitectum* Berk. & Rav. Booth and Sutton (in *Fusarium pallidoroseum*, the Correct Name for *F. semitectum* Auct., Trans. Br. Mycol. Soc. 83 (4): 702–704, 1984) indicated this binomial was invalid and showed that the correct name for this fungus is *F. pallidoroseum*. None of the known strains of *F. pallidoroseum* have been reported to produce cyclic tetrapeptides.

DESCRIPTION OF A SECOND PRODUCING ORGANISM

Compounds Ia, Ib, Ic, Ie, If and Ig are also produced by a novel *Fusarium sp.* (MF6058) isolated from the internal cortex of living roots of *Languncularia racemosa* (Combretaceae), collected in the Mangrove of the Rincón River, Osa Peninsula, Puntarenas Province, Costa Rica. A culture of this organism has been deposited with the American Type Culture Collection (Rockville, Md., USA) on Jan. 26, 1995 under the BUDAPEST TREATY ON THE INTERNATIONAL RECOGNITION OF THE DEPOSIT OF MICROORGANISMS FOR THE PURPOSES OF PATENT PROCEDURE and assigned the accession number ATCC 74322.

Colonies grew slowly on YM agar (Difco Laboratories), attaining 20–21 mm in diameter after 9 days at 25° C., 12 hr photoperiod. The colonies were slightly raised, zonate, moist, with abundant pale cream colored conidial masses accumulating in the oldest regions (Cream Color, Light Buff), with scant aerial mycelium, felty, margin white, even. Reverse was white to dull cream colored or pale yellow (Pale Ochraceous-Buff, Warm Buff). Exudates and odors were absent. No growth on YM agar at 37° C.

Colonies grew slowly on potato-dextrose agar (Difco Laboratories), attaining 22–24 mm in diameter after 10 days at 25° C., 12 hr photoperiod. The colonies were appressed, obscurely zonate, moist, waxy, with very scant aerial mycelium, translucent to pale grayish yellow (Cream Color, Light Buff). Reverse was similar in color. Exudates and odors absent.

Colonies grew slowly on SNA (Spezieller-N ährstoffarmer Agar, Nirenberg, H. 1976. Untersuchengen über die morphologische und biologische Differenzienrung in der Fusarium-Sektion Liseola. Mitt. Biol. Bundesanst. Land-Forstwirtsch. Berlin-Dahlem 169: 1–117), attaining 25 mm in diameter after 9 days at 25° C., 12 hr photoperiod. The colonies were appressed, azonate, with scant aerial mycelium, translucent, colorless, margin even, submerged. Reverse was translucent. Exudates and odors absent.

Micromorphology of the organism was evaluated on SNA and cornmeal dextrose agar (Difco Laboratories) and the following observations were made:

Conidial states were of two types; a scant, transient microconidial state formed on the aerial mycelium; and an abundant macroconidial state formed on the surface of the agar.

Macroconidial state: Conidia abundant in scattered to confluent, hyaline to cream colored sporodochia or pionnotes. Conidiophores arising from surface of agar, micronematous or semi-macronematous, consisting of aggregations of unbranched single conidiogenous cells or sparsely branched, fasiculate conidiophores, with each branch of conidiophores terminating as an individual conidiogenous cell. Conidiogenous cells phialidic, cylindrical or tapered towards apex, often with an inflated base, aseptate, 9–30 µm long, 1.5–2.5 µm wide at the tip, terminating in a broad conidiogenous locus, with distinct periclinal thickenings, often with a flared collarette. Conidia fusoid in face view, in side view straight in central portion with slightly curved ends, usually with a slightly protruding foot cell, with apical cell tapered to a curved rounded apex, but with distal and foot cell often difficult to distinguish due to symmetry of conidia in side view, overwhelmingly 3-septate, 4-, 2- or 1-septate conidia rarely observed, 35–47×6–9 µm, with refractive cytoplasmic contents, hyaline. Germination of single conidia occurred within 8–24 hr on cornmeal dextrose agar, with first germ tube usually protruding from foot cells, and second germ tube from apical cells.

Microconidial state: Conidiophores Verticillium-like, consisting of one or two whorls of verticillately arranged conidiogenous cells, infrequent and scattered on young aerial mycelium. Conidiogenous cells phialidic, cylindrical or awl-shaped, up to 10 µm long. Conidia narrowly ellipsoidal, 2–3×1.5–2 µm, hyaline.

Chlamydospores, sclerotia or teleomorph were not observed, even in cultures incubated up to 6 weeks.

This fungus is assigned the anamorph genus Fusarium because it produces moist, fusoid, curved, septate conidia from phialidic conidiogenous cells. The conidia have a foot cell, and thus MF6058 is best placed in Fusarium, rather than in Cylindrocarpon. Placement of this strain within the genus Fusarium is difficult because of its decided lack of diagnostic morphological features and its lack of pigments. This isolate possibly belongs in the Section Martiella of Fusarium (as defined by C. Booth. 1971. The genus Fusarium. Commonwealth Mycological Institute, Kew, U.K., pg. 44), due to its large, often unbranched conidiogenous cells, macroconidia with blunt rounded apices, verticillate microconidial state, and pale coloration. However, this strain exhibits several atypical features for this group Fusarium spp., typified by the well-known, $F.$ $solani,$ in that it does not form chlamydospores, the microconidial state is extremely reduced, and that the macroconidia are relatively short and uniform in size.

It is to be understood that the present invention is not limited to the use of the particular strain of Fusarium pallidoroseum or Fusarium sp. (MF6058), or to organisms fully answering the above descriptions, but includes any $F.$ pallidoroseum or strains of Fusarium capable of producing a compound of formula I. It is especially intended to include other strains or mutants or variants of said organisms which can be produced from the described organisms by known means such as X-ray radiation, ultraviolet radiation, treatment with nitrogen mustard, phage exposure, and the like, and which are capable of producing a compound of the present invention.

FERMENTATION OF THE PRODUCING ORGANISM

Compounds of formula I are produced by cultivating a strain of Fusarium pallidoroseum capable of producing said compound on a conventional solid medium or in a conventional aqueous medium. The organism is grown in a nutrient medium containing known nutritional sources for similar fungi, i.e. assimilable sources of carbon and nitrogen plus optional inorganic salts and other known growth factors. The general procedures used for the cultivation of other similar fungi are applicable to the present invention.

The nutrient medium should contain an appropriate assimilable carbon source such as ribose, glucose, sucrose, cellobiose and fructose. As nitrogen source, ammonium chloride, ammonium sulfate, urea, ammonium nitrate, sodium nitrate, etc. may be used either alone or in combination with organic nitrogen sources such as peptone, fish meal extract, yeast extract, corn steep liquor, soybean powder, cotton seed flour, etc. There may also be added, if necessary, nutrient inorganic salts to provide sources of sodium, potassium, calcium, ammonium, phosphate, sulfate, chloride, bromide, carbonate, zinc, magnesium, manganese, cobalt, iron, and the like.

Production of compounds of formula I may be effected at any temperature conducive to satisfactory growth of the producing organism, e.g. 20°–30° C. For Fusarium pallidoroseum ATCC 74289, the production temperature is preferably below about 25° C.; more preferably at about 20°–22° C. Ordinarily, optimum production of the desired compound is obtained in shake flasks after incubation periods of 10–21 days. Aeration in shake flasks is achieved by agitation, e.g. shaking on a rotary shaker. If fermentation is to be carried out in tank fermentors, it is desirable to produce a vegetative inoculum in a nutrient broth by inoculating the broth culture from a slant culture or a lyophilized culture of the organism. After obtaining an active inoculum in this manner, it is aseptically transferred to the fermentation tank medium. Production of the desired compound in tank fermentors usually reaches the optimum after 7 to 21 days of incubation. Agitation in the tank fermentor is provided by stirring and aeration may be achieved by injection of air or oxygen into the agitated mixture. Compound production may be monitored using chromatographic or spectroscopic techniques, or by a conventional biological assay.

In a preferred embodiment, the producing strain is *Fusarium pallidoroseum* having the identifying characteristics of ATCC 74289, or a mutant or a variant thereof. More preferably the producing strain is *Fusarium pallidoroseum* having the identifying characteristics of ATCC 74289. In another preferred embodiment, the fermentation is preferably carried out on a solid medium such as vermiculite.

Compounds Ia, Ib, Ic, Ie, If and Ig are also produced by *Fusarium sp.* having the identifying characteristics of ATCC 74322, which is a better producer of Compound Ia than *Fusarium pallidoroseum* (ATCC 74289).

ISOLATION AND PURIFICATION OF COMPOUND

Compounds of formula I are readily recovered from fermentation broth by extracting the whole broth with an organic solvent such as methyl ethyl ketone. The compounds may be purified using standard methods well known in the art such as gel filtration chromatography, thin layer chromatography, high performance liquid chromatography, concentration, precipitation and/or crystallization, or combinations thereof. Alternatively, the whole broth or an organic extract thereof may be spray-dried or freeze-dried, followed by purification as above mentioned.

Compounds of formula I wherein $R^2$ is —$OCH_3$ may be converted to the compounds of formula I wherein $R^2$ is H by conventional methods such as hydrogenolysis in the presence of a catalyst such as palladium on carbon.

UTILITY

The cyclic tetrapeptides of the present invention are useful as antiprotozoal agents. As such, they may be used in the treatment and prevention of protozoal diseases in human and animals, including poultry. Examples of protozoal diseases against which compounds of formula I may be used, and their respective causative pathogens, include: 1) amoebiasis (*Dientamoeba sp., Entamoeba histolytica*); 2) giardiasis (*Giardia lamblia*); 3) malaria (*Plasmodium species* including *P. vivax, P. falciparum, P. malariae* and *P. ovale*); 4) leishmaniasis (*Leishmania species* including *L. donovani, L. tropica, L. mexicana,* and *L. braziliensis*); 5) trypanosomiasis and Chagas disease (*Trypanosoma species* including *T. brucei, T. theileri, T. rhodesiense, T. gambiense, T. evansi, T. equiperdum, T. equinum, T. congolense, T. vivax* and *T. cruzi*); 6) toxoplasmosis (*Toxoplasma gondii*); 7) babesiosis (*Babesia sp.*); 8) cryptosporidiosis (*Cryptosporidium sp.*); 9) dysentary (*Balantidium coli*); 10) vaginitis (*Trichomonas species* including *T. vaginitis,* and *Tritrichomonas foetus*); 11) coccidiosis (*Eimeria species* including *E. tenella, E. necatrix, E. acervulina, E. maxima* and *E. brunetti, E. mitis, E. bovis, E. melagramatis,* and *Isospora sp.*); 12) enterohepatitis (*Histomonas gallinarum*), and 13) infections caused by *Anaplasma sp., Besnoitia sp., Leucocytozoan sp., Microsporidia sp., Sarcocystis sp., Theileria sp.,* and *Pneumocystis carinii.*

Compounds of formula I are preferably used in the treatment or prevention of malaria, toxoplasmosis, cryptosporidiosis and trypanosomiasis in humans and animals; and in the management of coccidiosis, particularly in poultry, either to treat coccidial infection or to prevent the occurrence of such infection.

DOSE RANGE

Compounds of formula I may be administered to a host in need of treatment in a manner similar to that used for other antiprotozoal agents; for example, they may be administered parenterally, orally, topically, or rectally. The dosage to be administered will vary according to the particular compound used, the infectious organism involved, the particular host, the severity of the disease, physical condition of the host, and the selected route of administration; the appropriate dosage can be readily determined by a person skilled in the art. For the treatment of protozoal diseases in humans, the oral dosage may range from 1 mg/kg to 1000 mg/kg; and the parenteral dosage may range from 0.5 mg/kg to 500 mg/kg. For veterinary therapeutic use, the oral dosage may range from 1 mg/kg to 1000 mg/kg; and the parenteral dosage may range from 0.5 mg/kg to 500 mg/kg. For prophylactic use in humans, the oral dosage may range from 1 mg/kg to 1000 mg/kg; and the parenteral dosage may range from 0.5 mg/kg to 500 mg/kg. For prophylactic use in animal, the oral dosage may range from 1 mg/kg to 1000 mg/kg; and the parenteral dosage may range from 0.5 mg/kg to 500 mg/kg. For use as an anticoccidial agent, particularly in poultry, the compound is preferably administered in the animals' feed or drinking water. The dosage ranges s from 1 mg/kg to 1000 mg/kg

COMPOSITION

The compositions of the present invention comprises a compound of formula I and an inert carrier. The compositons may be in the form of pharmaceutical compositions for human and veterinary usage, or in the form of feed composition for the control of coccidiosis in poultry.

The pharmaceutical compositions of the present invention comprise a compound of formula I as an active ingredient, and may also contain a pharmaceutically acceptable carrier and optionally other therapeutic ingredients. The compositions include compositions suitable for oral, rectal, topical, and parenteral (including subcutaneous, intramuscular, and intravenous) administrations, although the most suitable route in any given case will depend on the particular host, and nature and severity of the conditions for which the active ingredient is being administered. The pharmaceutical compositions may be conveniently presented in unit dosage form and prepared by any of the methods well-known in the art of pharmacy.

In practical use, compounds of formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous).

In preparing the compositions for oral dosage form, any of the usual pharmaceutical media may be employed. For example, in the case of oral liquid preparations such as suspensions, elixirs and solutions, water, glycols, oils, alcohols, flavoring agents, preservatives, coloring agents and the like may be used; or in the case of oral solid preparations such as powders, capsules and tablets, carriers such as starches, sugars, microcrystalline cellulose, diluents, granulating agents, lubricants, binders, disintegrating agents, and the like may be included. Because of their ease of administration, tablets and capsules represent the most advantageous oral dosage unit form in which case solid pharmaceutical carriers are obviously employed. If desired, tablets may be coated by standard aqueous or nonaqueous techniques. In addition to the common dosage forms set out above, compounds of formula I may also be administered by controlled release means and/or delivery devices.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

Pharmaceutical compositions of the present invention suitable for parenteral administration may be prepared as solutions or suspensions of these active compounds in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Suitable topical formulations include transdermal devices, aerosols, creams, ointments, lotions, dusting powders, and the like. These formulations may be prepared via conventional methods containing the active ingredient. To illustrate, a cream or ointment is prepared by mixing sufficient quantities of hydrophilic material and water, containing from about 5–10% by weight of the compound, in sufficient quantities to produce a cream or ointment having the desired consistency.

Pharmaceutical compositions suitable for rectal administration wherein the carrier is a solid are most preferably presented as unit dose suppositories. Suitable carriers include cocoa butter and other materials commonly used in the art, and the suppositories may be conveniently formed by admixture of the combination with the softened or melted carrier(s) followed by chilling and shaping moulds.

It should be understood that in addition to the aforementioned carrier ingredients the pharmaceutical formulations described above may include, as appropriate, one or more additional carrier ingredients such as diluents, buffers, flavoring agents, binders, surface-active agents, thickeners, lubricants, preservatives (including anti-oxidants) and the like, and substances included for the purpose of rendering the formulation isotonic with the blood of the intended recipient.

For use in the management of coccidiosis in poultry, a compound of formula I may be conveniently administered as a component of a feed composition. Suitable poultry feed composition will typically contain from about 1 ppm to about 1000 ppm, preferably from about 0.01% to about 0.1% percent, by weight of a compound of formula I. The optimum levels will naturally vary with the species of Eimeria involved, and can be readily determined by one skilled in the art. Levels of in poultry feed of from about 0.01% to about 0.1% percent by weight of the diet are especially useful in controlling the pathology associated with E. tenella, while the preferred concentration for similar control of intestinal-dwelling species is from about 0.01% to about 0.1% percent by weight of the diet. Amounts of about 0.01% to about 0.1% percent by weight are advantageous in reducing the pathogenic effects of both cecal and intestinal coccidiosis.

In the preparation of poultry feed, a compound of formula I may be readily dispersed by mechanically mixing the same in finely ground form with the poultry feedstuff, or with an intermediate formulation (premix) that is subsequently blended with other components to prepare the final poultry feedstuff that is fed to the poultry. Typical components of poultry feedstuffs include molasses, fermentation residues, corn meal, ground and rolled oats, wheat shorts and middlings, alfalfa, clover and meat scraps, together with mineral supplements such as bone meal, calcium carbonate and vitamins.

Compositions containing a compound of formula I may also be prepared in powder or liquid concentrate form. In accordance with standard veterinary formulation practice, conventional water soluble excipients, such as lactose or sucrose, may be incorporated in the powders to improve their physical properties. Thus particularly suitable powders of this invention comprise 50 to 100% w/w, and preferably 60 to 80% w/w of the combination and 0 to 50% w/w and preferably 20 to 40% w/w of conventional veterinary excipients. These powders may either be added to animal feedstuffs, for example by way of an intermediate premix, or diluted in animal drinking water.

Liquid concentrates of this invention suitably contain a water-soluble compound combination and may optionally include a veterinarily acceptable water miscible solvent, for example polyethylene glycol, propylene glycol, glycerol, glycerol formal or such a solvent mixed with up to 30% v/v of ethanol. The liquid concentrates may be administered to the drinking water of animals, particularly poultry.

The following examples are provided to more fully illustrated the present invention, and are not be construed as limiting the scope of the claims in any manner.

EXAMPLE 1

Production of Tetrapeptide of Formula Ia (a) seed culture of *Fusarium pallidoroseum*

A portion of agar slant containing *Fusarium pallidoroseum* ATCC 74289 was aseptically transferred to a 250 mL unbaffled flask containing 50 mL of seed medium having the following composition:

Yeast extract (Difco) 4.0 g/L

Malt extract (Difco) 8.0 g/L

Glucose 4.0 g/L

Junlon (polyacrylic acid, Kouyok Trading Co., Tokyo) 1.5 g/L distilled water q.v. 1 L pH adjusted to 7.0 prior to sterilization.

The culture was incubated on a 2-inch throw gyratory shaker, (220 rpm) for 2 days at 25° C., 85% relative humidity (rh), to obtain biomass. Portions of the biomass were transferred into sterile vials containing glycerol and frozen (as frozen vegetative mycelia). These were maintained in a final concentration of 10–15% glycerol at −75° C.

A vial of the above frozen vegetative mycelia was thawed to room temperature and used to inoculate the seed medium (1 mL per mL seed medium), and the culture was incubated under the conditions described above.

Seed culture of *Fusarium pallidoroseum* ATCC 74289 may also be prepared under conditions similar to those described above in the medium having the composition provided in Example 7(a).

(b) production culture of *Fusarium pallidoroseum*

An aliquot of the seed culture (12 mL, in the above seed medium) was placed into 220 mL of the liquid portion of the production medium having the following composition:

Glucose 150.0 g/L

Fructose 15.0 g/L

Sucrose 40.0 g/L

NZ amine Type E (Sheffield Products) 4.0 g/L

Urea 4.0 g/L $K_2HPO_4$ 0.5 g/L

KCl 0.25 g/L $MgSO_4 \cdot 7H_2O$ 0.25 g/L $ZnSO_4 \cdot 7H_2O$ 0.9 g/L $CaCO_3$ 8.0 g/L distilled water q.v. 1 L (pH7.0)

This mixture was swirled vigorously to disperse the biomass and then poured into a 2-liter roller culture vessel which contained 675 cubic centimeters of steam-sterilized large-particle vermiculite (the solid portion). The contents of the roller bottle were shaken/mixed to insure homogeneous inoculation and coverage. The roller bottles were incubated horizontally, revolving at approximately 4 rpm on a Wheaton roller apparatus, at 22° C., 75% rh for 19 days, to obtain secondary metabolite production in the fermentation medium.

(c) alternative production culture of *Fusarium pallidoroseum*

Sterilized vermiculite (50 cc) in 250 mL unbaffled flask was fortified with 20 mL of the liquid portion of the above production medium, and inoculated with 2 mL of the seed culture (prepared in either medium of Example 1(a) or Example 7(a)). The flask was incubated at 22° C., 70% rh for 10 days.

EXAMPLE 2

Isolation and Purification of Tetrapeptide of Formula Ia (Method A)

The fermentation broth obtained from the production culture of Example 1 was extracted with methyl ethyl ketone (MEK). A 100 ml portion of the extract was concentrated to dryness under reduced pressure and the residue was dissolved in 8 ml of methylene chloride-methanol 1:1. A first fractionation was achieved by gel filtration on a 150 ml Sephadex LH-20 (Pharmacia) column packed in, and washed with, methanol, which afforded bioactive material after 0.6–0.65 column volumes of elution. Preparative thin layer chromatography (TLC) on a E. Merck silicagel $60_{F254}$ plate, 20×20 cm, 250 mm thickness, eluted with methylene chloride-methanol 93:7 (v/v), was used next for purification. This process yielded the target compound at Rf 0.7–0.8.

Final purification was accomplished by preparative high performance liquid chromatography (HPLC) on a 9 mm×25 cm Zorbax $RxC_8$ column eluted at 50° C. and 4 ml/minute with 60-minute gradient of 40% to 60% acetonitrile in water. The compound Ia (2.5 mg) was obtained in fractions corresponding to a k' of 8; its homogeneity was ascertained in several TLC systems on both silicagel $60_{F254}$ and Whatman $KC_{18}$ plates; by NMR in $CD_2Cl_2$; and by HPLC (Zorbax $RxC_8$, 4.6×250 mm, 60% acetonitrile, 50° C., k'=5.5).

EXAMPLE 3

Isolation and Purification of Tetrapeptide of Formula Ia (Method B)

The fermentation broth (1.6 L) prepared as in Example 1 was extracted with MEK. After evaporating the solvent, the residual aqueous suspension was freeze-dried. The resulting solid mass was extensively triturated with methylene chloride and filtered. The solution was first fractionated at high speed on a 100 ml bed of dry E. Merck silicagel 60 using methylene chloride-methanol 97:3 (v/v). The enriched material thus obtained was further purified on a 100 ml silicagel column, eluting with methylene chloride-ethyl acetate 3:1 (v/v), which gave homogenous compound Ia after 5–6.5 column volumes of elution. Yield of pure material: 85% of the amount present in the original extract.

EXAMPLE 4

Characterization of the Tetrapeptide of Formula Ia

The structure of the cyclic tetrapeptide of formula Ia, isolated from the fermentation broth of *Fusarium pallidoroseum* ATCC 74289, was determined using various spectroscopic techniques including nuclear magnetic resonance (NMR) and mass spectroscopy (MS).

NMR spectra were measured on a Varian Unity 400 spectrometer, in d-5 pyridine $^{13}C$ NMR (δ, ppm) 8.40, 11.40, 16.26, 20.44, 24.22, 25.14, 25.59, 26.25, 26.25, 26.47, 29.32, 30.71, 35.85, 36.04, 42.44, 44.64, 51.35, 54.87, 55.28, 62.08, 66.10, 108.72, 109.32, 119.86, 120.63, 123.28, 123.31, 124.60, 133.38, 172.90, 174.90, 175.25, 177.00, 210.77.

$^1H$ NMR (δ, ppm) 0.94 (t, J=7.2 Hz), 1.00 (t, J=7.6 Hz), 1.00 (d, J=7.2 Hz), 1.10 (m), 1.25 (m), 1.25 (m), 1.30 (m), 1.40 (m), 1.44 (m), 1.45 (m), 1.48 (m), 1.50 (m), 1.60 (m), 1.80 (m), 1.90 (m), 2.10 (m), 2.18 (t, J=7.2 Hz), 2.28 (q, J=7.2 Hz), 2.42 (m), 3.27 (dt, 13.2, 2.4 Hz), 3.84 (dd, J=14.4, 6.4 Hz), 3.94 (s), 4.23 (dd, J=14.4, 10.4 Hz), 4.37 (brd, J=12.0 Hz), 4.61 (td, J=10.6, 6.4 Hz), 4.76 (brq, J=8.0 Hz), 5.18 (t, J=10 Hz), 5.53 (brd, J=5.6 Hz), 7.18 (dt, J=8.0, 0.8 Hz), 7.34 (dt, J=8.0, 0.6 Hz), 7.36 (d, J=10 Hz), 7.55 (d, J=8.0 Hz), 7.58 (s), 7.79 (d, J=8.0 Hz), 8.27 (d, J=10.4 Hz), 10.03 (d, J=6.8 Hz).

Mass spectra were recorded on Jeol SX-102A (electron impact, EI,90eV) and JEOL HX110 (Fast Atom Bombardment, FAB) mass spectrometers. Exact mass measurements were performed at high resolution (HR-EI) using perfluorokerosene (PFK) as internal standards. Trimethylsilyl derivatives were prepared with a 1:1 mixture of bis(trimethylsilyl)trifluoroacetamide (BSTFA)-pyridine at room temperature. The FAB spectrum was run in a matrix of dithiothreitol dithioerthritol (20/80). The molecular ion is observed by electron impact MS at m/z 623. It was found to form a strong monotrimethylsilyl derivative. The molecular formula was determined by scanning high resolution electron impact MS to be $C_{34}H_{49}N_5O_6$ (found 695.4090, calculated 695.4077 for $C_{34}H_{49}O_6N_5+C_3H_8Si$; found 623.3738, calc. for $C_{34}H_{49}N_5O_6$ 623.3683 $M^+$).

The stereochemistry of compound Ia was determined by hydrolysis and subsequent analysis of AMBI ($\alpha$-methylbenzylisocyanate) derivatives of the derived amino acids. Only the stereochemistry of isoleucine and tryptophan could be determined with certainty by this method and they were found to have L stereochemistry. The stereochemistry of pipecolic acid and $\alpha$-amino-8-oxo-decanoic acid was determined by using $^1$H NMR coupling constant and NOE (nuclear Overhauser effect) measurements of intact compound Ia. A similar hydrolysis of compound Ih (derived from compound Id) gave D-pro, L-isoleucine and L-tryptophan.

EXAMPLE 5

Antiprotozoal Activity of Tetrapeptide of Formula Ia

Compound of formula Ia was evaluated against *Eimeria tenella*, *Toxoplasma gondii*, and *Plasmodium falciparum* according to methods reported in the literature.

(A) Activity against *E. tenella*

The visual assay using Madin Darby bovine kidney (MDBK) cell line as described in Schmatz, Crane and Murray, "*Eimeria tenella*: Parasite-Specific Incorporation of $^3$H-Uracil as a Quantitative Measure of Intracellular Development" *J. Protozoology*, 1986, 33(1):109–114 was generally followed to evaluate the compound's anti-Eimeria activity. In this assay, the compound showed a miminum inhibitory concentration of 15 ng/ml.

(B) Activity against *T. gondii*

The visual assay described in Roos et al, In: "Methods in Microbial Pathogenesis", *Methods in Cell Biology*, 1994, D. G. Russell, Ed., (Academic Press) was generally followed to evaluate the compound's anti-Toxoplasma activity. In this assay, the compound showed a miminum inhibitory concentration of 0.05–0.1 ng/ml.

(C) Activity against *P. falciparum*

The antimalarial activity was determined in a radioactive assay following the general protocol described in Desjardins et al, "Quantitative Assessment of Antimalarial Activity In Vitro by a Semiautomated Microdilution Technique" *Antimicrobial Agents and Chemotherapy*, 1979, 16:710–718. In this assay, the compound showed an $IC_{50}$ (the concentration of drug which inhibits the parasite specific uptake of radiolabel by 50%) of 54 ng/ml.

EXAMPLE 6

Preparation of Tetrapeptide of Formula Ib

To a solution of the tetrapeptide of formula Ia (2.8 mg) in a 2 mL (1:1) mixture of methanol and ethyl acetate was added 10% palladium over charcoal (5 mg) and the mixture was evacuated to remove dissolved air. This mixture was flushed with hydrogen and this degassing and flushing cycle was repeated three times. Finally the hydrogen was connected to the flask containing the reaction mixture, and the mixture was stirred for 2 hrs. The catalyst was removed by filtration through celite and the filtrate was evaporated under reduced pressure to give 2.6 mg of the title compound as a colorless powder.

$^1$H NMR ($CD_2Cl_2$): 0.86 (3H, d, J=6.4 Hz), 0.94 (3H, t, J=7.2 Hz), 1.05 (3H, t, J=7.6 Hz), 1.10–1.70 (13H, m), 1.78 (1H, m), 1.99 (1H, m), 2.01 (1H, m), 2.15 (1H, m), 2.38 (2H, dt, J=7.2, 1.2 Hz), 2.43 (2H, q, J=7.6 Hz), 3.10 (1H, dt, J=13.6, 3.2 Hz), 3.48 (1H, dd, J=14.4, 6.4 Hz), 3.70 (1H, dd, J=14.6, 10.0 Hz), 3.99 (1H, m), 4.04 (1H, m), 4.18 (1H, dd, J=10.6, 8.8, 7.0 Hz), 4.69 (1H, t, J=10.4 Hz), 5.06 (1H, brd, J=5.2 Hz), 6.36 (1H, d, J=5.6 Hz), 6.41 (1H, d, J=10.4 Hz), 6.99 (1H, d, J=10.4 Hz), 7.10 (1H, brs), 7.12 (1H, ddd, J=8.0, 6.8, 0.8 Hz), 7.18 (1H, ddd, J=8.4, 7.2, 1.2 Hz), 7.39 (1H, dt, J=8.4, 1.2 Hz), 7.60 (1H, dd, J=7.6, 0.4 Hz), 8.67 (1H, brs); HREI-MS (m/z): $M^+$ 593.3610 (calc. for $C_{33}H_{47}N_5O_5$ 593.3577).

EXAMPLE 7

Production of Tetrapeptide Ia using *Fusarium sp.* ATCC 74322

(a) seed culture of *Fusarium sp.* ATCC 74322

A portion of agar slant containing *Fusarium sp.* ATCC 74322 was aseptically transferred to a 250 mL unbaffled flask containing 50 mL of the seed medium of EXAMPLE 1(a)

The culture was incubated on a 2-inch throw gyratory shaker, (220 rpm) for 3 days at 25° C., 85% relative humidity (rh), to obtain biomass. Portions of the biomass were transferred into sterile vials containing glycerol and frozen (as frozen vegetative mycelia). These were maintained in a final concentration of 10–15% glycerol at –75° C.

A vial of the above frozen vegetative mycelia was thawed to room temperature and used to inoculate the seed medium (1 mL per 50 mL seed medium), and the culture was incubated for 2–4 days under the conditions described above. Seed medium of the following composition may also be used to prepare the seed culture:

Corn steep liquor 5.0 g/L

Tomato paste 40.0 g/L

Oat flour 10.0 g/L

Glucose 10.0 g/L

Trace element mix* 10 mL/L distilled water q.v. 1 L pH adjusted to 6.8 prior to sterilization.

*composition (g/L)=$FeSO_4.7H_2O$ (1.0); $MnSO_4.4H_2O$ (1.0); $CuCl_2.H_2O$ (0.025); $CaCl_2$ (0.1); $H_3BO_3$ (0.056); $(NH_4)_6MoO_2.4H_2O$ (0.019); $ZnSO_4.7H_2O$ (0.2).

(b) production culture of *Fusarium sp.*

An aliquot of the seed culture (12 mL) was placed into 220 mL of the liquid portion of the production medium having the following composition:

Glucose 150.0 g/L

NZ amine Type A (Sheffield Products) 4.0 g/L

Urea 4.0 g/L $K_2HPO_4$ 0.5 g/L

KCl 0.25 g/L $MgSO_4.7H_2O$ 0.25 g/L $ZnSO_4.7H_2O$ 0.9 g/L $CaCO_3$ 16.5 g/L distilled water q.v. 1 L (pH7.0)

This mixture was swirled vigorously to disperse the biomass and then poured into a 2-liter roller culture vessel which contained 675 cubic centimeters of steam-sterilized large-particle vermiculite (the solid portion). The contents of the roller bottle were shaken/mixed to insure homogeneous inoculation and coverage. The roller bottles were incubated horizontally, revolving at approximately 4 rpm on a Wheaton roller apparatus, at 22° C., 75% rh for 24 days, to obtain secondary metabolite production in the fermentation medium.

The culture also produced the desired metabolites in liquid medium (50 mL in 250 mL unbaffled flask) containing the liquid portion of the above production medium. The flasks were incubated at 22° C., 75% rh for 7–14 days.

Fermentation batches in 23 L tank fermentor and 800 L vessels were also carried out using the above liquid production medium. For the 23 L tank, 10 L of the production medium plus 10 mL of P-2000 (polyethylene glycol, Dow Chemical) was inoculated with 500 mL of the seed culture, and the fermentation carried out at 21° C., with agitation set at 400 rpm, air flow at 5 L/min and pressure at 0.3 bar. The agitation was increased to 500 and then 600 rpm, and air flow to 10 L/min on day 6 of fermentation (day 0 being the day fermentation started). The fermentation broth was harvested after 14 days for product isolation. For the 800 L vessel, 550 L of the production medium plus 2 mL/L of P-2000 were inoculated with 25 L of the seed culture. The fermentation was carried out at 21° C., pressure of 0.7 kg/cm2, air flow rate of 250 standare liter/min., and agitator speed of 250 rpm, which increased automatically to maintain a minimum dissolved oxygen tension of 50% of atmospheric saturation). The broth was harvested after 175 hours.

The same 23 L tank conditions were also applied in fermentation using the production medium whose composition is given in Example 1(b).

EXAMPLE 8

Isolation and Purification of Compound Ia from fermentation of *Fusarium sp.* ATCC 74322

Methylethyl ketone extract (100 mL) of a fermentation of *Fusarium sp.* ATCC 74322, prepared in roller bottles as described in Example 7 and extracted as described in Example 3, was evaporated down and fractionated by gel filtration on a 150 cc Sephadex LH-20 column in methanol. This afforded an enriched preparation of Compound Ia after 0.6 column volumes of washing. Final purification could be achieved by column chromatography on EM silica gel using ethyl acetate in methylene chloride as eluent (1:2 v/v). Yield: approx. 5 mg of homogeneous material.

EXAMPLE 9

Isolation and Purification of Minor Components

Fermentation broth (5.6 liters), prepared as in Example 1, containing 225 mg of compound Ia, was extracted with methylethyl ketone by stirring for 2 hours and filtering off the spent biomass. After evaporating the solvent under reduced pressure and freeze-drying the resulting aqueous suspension, the semi-solid residue obtained was taken up in 200 ml of methylene chloride and filtered to remove large amounts of insoluble, unrelated materials.

The solution was again evaporated down and the new residue dissolved in methanol. Fractionation proceeded by gel filtration on a 950 cc column of Sephadex LH-20 in methanol, whereupon compound Ia and several related analogs eluted after 0.55–0.65 column volumes. There followed a flash chromatography step on a 120 cc E. Merck silica gel 60 column eluted with a step gradient of methanol in methylene chloride. The target compounds again eluted together, in fractions corresponding to the 3% methanol washings.

Material from the first silica gel column was put through a new 120 cc E. Merck silica gel 60 column, this time eluting with a methylene chloride-ethyl acetate 3:1 v/v mixture, and gradually increasing the ethyl acetate content to 100%. This process afforded four fractions, in order of elution,
I. a>90% pure preparation of compound Ia,
II. a fraction containing a 1:1 mixture of compound Ia and minor component compound Ic,
III. a mixture of compounds Ib, Id and Ie,
IV. an enriched preparation of minor compound If.

Fraction II was further processed by preparative TLC on E.M. silica gel $60_{F254}$ 0.25 mm thickness plates developed with hexane-acetone 2:1 v/v; this led to the separation of the remnants of compound Ia from minor compound Ic. The latter was finally purified by HPLC on a 9×250 mm Zorbax $RxC_8$ column, maintained at 50° C., using a gradient of acetonitrile in water (30% to 60% over 120 minutes) delivered at 2 ml/minute. Compound Ic eluted after 4.6–5.0 column volumes of washing and was pure by all analytical methods.

Fraction III was directly processed by HPLC (same conditions as above). Homogenous compound Id was found after 15.5 minutes into the gradient; minor compound Ib eluted 18 minutes into the gradient; and compound Ie at 20.5 minutes.

Fraction IV, on the other hand, was judged to be still too complex for successful HPLC. Accordingly, it was first further enriched by gel filtration on Sephadex LH-20 before final purification of compound If by HPLC (9×250 mm Zorbax $RxC_8$ column, maintained at 50° C., eluted isocratically for 1 hour with 2 ml/minute 30% aqueous acetonitrile, followed by a 2-hour gradient to 60% acetonitrile). Ve=6.9–7.2 column volumes.

The minor components were present at 0.25–1% of the content of compound Ia.

EXAMPLE 10

Isolation and Purification of Minor Component Ig

It was only during yet another scaled up purification process that compound Ig was discovered. Ten liters of fermentation broth were processed through extraction and the two silica gel steps described in Example 9. The latest minor analog was detected in the latter part of the methylene chloride-ethyl acetate 1:3 washings. Preparative TLC on EM silica gel $60_{F254}$ plates with methylene chloride-methanol 96:4 v/v, and a final purification by HPLC (9×250 mm Zorbax $RxC_8$ column, maintained at 50° C., elution with 2 ml/minute acetonitrile-water 40:60 v/v) yielded 1.2 mg of compound Ig, i.e. <0.1% of the content of compound Ia in broth.

Homogeneity of all the preparations was ascertained in several TLC systems (silica gel $60_{F254}$ with methylene chloride-ethyl acetate 1:1; methylene chloride-methanol 97:3; hexane-acetone 2:1; Whatman $K_{C18}$ plates with methanol-water 85:15) and by HPLC (4.6×250 mm Zorbax $RxC_8$ column, 1 ml/minute acetonitrile-water 55:45, 50° C., UV detection at 222 nm):
Compound Ia: k'=7.8
Compound Ic k'=5.8
Compound Id k'=3.6
Compound Ie k'=4.9
Compound Ic k'=6.1
Compound If k'=3.7
Compound Ig k'=5.7

EXAMPLE 11

Spectroscopic Characterization of Minor Components

The NMR and MS data for the minor components, compounds Ic to Ig, are provided below. The NMR spectra were recorded either on a Varian Unity 400 or a 500 MHz NMR spectrometers. The MS spectra were obtained as previously described in Example 4.

Compound Ic $^{13}$C NMR (100 MHz, pyridine-$d_5$): 7.84, 18.63, 19.33, 19.88, 23.67, 25.55, 25.67, 25.67, 25.92, 28.74, 29.42, 30.12, 35.46, 41.86, 44.03, 50.74, 54.70, 55.73, 61.49, 65.45, 108.17, 108.74, 119.29, 120.07, 122.74, 122.74, 124.00, 132.82, 171.86, 174.24, 174.67, 176.44, 210.16.

$^{1}$H NMR (400 MHz, pyridine-$d_5$): 1.01 (3H, t, J=7.2 Hz), 1.02 (3H, d, J=7.6), 1.10 (2H, m), 1.16 (3H, d, J=6.8 Hz), 1.22 (2H, m), 1.25 (1H, m), 1.45 (3H, m), 1.49 (1H, m), 1.50 (1H, m), 1.60 (1H, m), 1.89 (1H, m), 2.07 (1H, m), 2.18 (2H, t, J=7.2 Hz), 2.28 (2H, q, J=7.6 Hz), 2.34 (1H, m), 2.58 (1H, m), 3.26 (1H, dt, J=13.2, 2.4 Hz), 3.82 (1H, dd, J=14.8, 6.4 Hz), 3.94 (3H, s), 4.25 (1H, dd, J=10.4, 14.4 Hz), 4.36 (1H, brd, J=13.6), 4.61 (1H, dt, J=10.8, 6.0 Hz), 4.75 (1H, appq, J=8 Hz), 5.08 (1H, t, J=10.4 Hz), 5.52 (1H, brd, J=5.2), 7.19 (1H, dt, J=8.0, 0.8 Hz), 7.32 (1H, d, J=10.5 Hz), 7.34 (1H, dt, J=8.0, 0.8 Hz), 7.55 (1H, d, J=8.0 Hz), 7.59 (1H, s), 7.80 (1H, d, J=8.0 Hz), 8.27 (1H, d, J=10 Hz), 10.03 (1H, d, J=6.8 Hz).

HR-EIMS (m/z): 609.3512 (M$^+$, calcd for $C_{33}H_{47}N_5O_6$: 609.3526).

Compound Id $^{13}$C NMR (100 MHz, pyridine-$d_5$): 8.03, 10.84, 15.84, 23.94, 25.03, 25.24, 25.40, 25.95, 25.95, 29.06, 30.42, 34.78, 35.72, 42.14, 46.90, 55.42, 58.03, 58.24, 61.95, 65.74, 108.44, 108.95, 119.56, 120.26, 122.85, 122.94, 124.32, 133.02, 172.04, 174.07, 175.18, 176.06, 210.47.

$^{1}$H NMR (400 MHz, pyridine-$d_5$): 0.92 (3H, t, J=7.2 Hz), 0.98 (3H, d, J=6.8 Hz), 1.01(3H, t, J=7.2), 1.10 (2H, m), 1.25 (2H, m), 1.35 (1H, m), 1.40 (2H, m), 1.65 (1H, m), 1.66 (1H, m), 1.78 (1H, m), 1.80 (1H, m), 1.90 (1H, m), 2.20 (2H, t, J=7.6 Hz), 2.28 (1H, m), 2.29 (2H, q, J=7.2 Hz), 2.36 (1H, m), 2.43(1H, m), 3.59 (1H, appq, J=8 Hz), 3.91 (1H, dd, J=14.4, 7.2 Hz), 3.94 (3H, s), 4.11 (1H, dt, J=10.0, 4.0 Hz), 4.23 (1H, dd, J=10.0, 14.8 Hz), 4.54 (1H, dt, J=9.6, 6.8 Hz), 4.74 (1H, brq, J=8.4 Hz), 4.91 (1H, t, J=10 Hz), 5.11 (1H, d, J=7.6 Hz), 7.19 (1H, t, J=8.0 Hz), 7.33 (1H, t, J=8.0 Hz), 7.55 (1H, d, J=8.0 Hz), 7.58 (1H, s), 7.78 (1H, d, J=8.0 Hz), 7.92 (1H, d, J=10.0 Hz), 8.33 (1H, d, J=10 Hz), 9.98 (1H, d, J=6.4 Hz).

HR-EIMS (m/z): 609.3525 (M$^+$, calcd for $C_{33}H_{47}N_5O_6$: 609.3526).

Compound Ie $^{13}$C NMR (100 MHz, pyridine-$d_5$): 10.59, 11.01, 15.86, 20.06, 24.74, 25.19, 25.86, 26.05, 26.19, 26.19, 29.69, 30.50, 31.00, 35.48, 37.71, 44.29, 50.99, 54.44, 55.14, 61.35, 65.70, 72.14, 108.31, 108.92, 119.47, 120.24, 122.83, 122.92, 124.23, 132.99, 172.07, 174.50, 174.83, 176.45.

$^{1}$H NMR (400 MHz, pyridine-$d_5$): 0.94 (3H, t, J=7.6 Hz), 1.00 (3H, d, J=6.8 Hz), 1.09 (3H, t, J=7.6), 1.30 (3H, m), 1.40 (5H, m), 1.44 (1H, m), 1.45 (2H, m), 1.48 (1H, m), 1.50 (1H, m), 1.60 (2H, quintet, J=7.6 Hz), 1.65 (1H, m), 1.85 (1H, m), 1.93 (1H, m), 2.06 (1H, brd, J=13.6), 2.32 (1H, m), 2.42 (1H, m), 3.27 (1H, dt, J=13.2, 2.0 Hz), 3.66 (1H, m), 3.86 (1H, dd, J=14.0, 6.4 Hz), 3.94 (3H, s), 4.23 (1H, dd, J=10.4, 14.4 Hz), 4.38 (1H, brd, J=13.6 Hz), 4.61 (1H, dt, J=10.4, 6.4 Hz), 4.79 (1H, brq, J=8.4 Hz), 5.19 (1H, t, J=10 Hz), 5.51 (1H, d, J=5.5 Hz, OH), 5.54 (1H, d, J=4.8 Hz), 7.19 (1H, t, J=8.0 Hz), 7.34 (1H, t, J=7.2 Hz), 7.37 (1H, d, J=9.6 Hz), 7.55 (1H, d, J=8.0 Hz), 7.58 (1H, s), 7.79 (1H, d, J=7.6 Hz), 8.28 (1H, d, J=10.0 Hz), 10.05 (1H, d, J=6.4 Hz).

HR-EIMS (m/z): 625.3802 (M$^+$, calcd for $C_{34}H_{51}N_5O_6$: 625.3839).

Compound If $^{13}$C NMR (125 MHz, pyridine-$d_5$): 11.00, 15.87, 20.06, 20.28, 23.55, 24.74, 25.20, 25.86, 25.92, 26.11, 29.06, 30.33, 35.47, 37.50, 44.26, 50.97, 54.47, 54.97, 61.57, 65.71, 73.41, 108.32, 108.94, 119.48, 120.25, 122.90, 122.93, 124.22, 133.01, 172.07, 174.50, 174.86, 176.53, 213.87.

$^{1}$H NMR (500 MHz, pyridine-$d_5$): 0.91 (3H, t, J=7.6 Hz), 0.97 (3H, d, J=6.8 Hz), 1.10 (2H, m), 1.25 (3H, m), 1.30 (1H, m), 1.35 (1H, m), 1.44 (3H, d, J=6.8 Hz), 1.45 (2H, m), 1.50 (2H, m), 1.60 (1H, m), 1.84 (2H, m), 2.05 (1H, brd, J=14.0), 2.30 (1H, m), 2.40 (1H, m), 2.56 (2H, dt, J=7.2, 1.2 Hz), 3.24 (1H, dt, J=11.2, 2.0 Hz), 3.82 (1H, dd, J=14.4, 6.4 Hz), 3.92 (3H, s), 4.20 (1H, dd, J=10.4, 14.4 Hz), 4.35 (1H, brd, J=12.8 Hz), 4.43 (1H, m), 4.58 (1H, dt, J=10.4, 6.4 Hz), 4.72 (1H, brq, J=7.2 Hz), 5.16 (1H, t, J=10.4 Hz), 5.50 (1H, d, J=5.6 Hz), 6.70 (1H, d, J=4.4 Hz, OH), 7.16 (1H, t, J=7.2 Hz), 7.30 (1H, t, J=8.0 Hz), 7.32 (1H, d, J=10.0 Hz), 7.52 (1H, d, J=8.0 Hz), 7.56 (1H, s), 7.76 (1H, d, J=8.0 Hz), 8.26 (1H, d, J=10.0 Hz), 9.95 (1H, d, J=6.4 Hz).

HR-EIMS (m/z): 639.3575 (M$^+$, calcd for $C_{34}H_{49}N_5O_7$: 639.3632).

Compound Ig $^{13}$C NMR (125 MHz, pyridine-$d_5$): 11.02, 15.88, 20.07, 24.35, 24.76, 25.21, 25.87, 26.06, 26.11, 26.30, 29.51, 29.82, 30.47, 35.48, 40.14, 44.27, 50.98, 54.49, 55.00, 61.64, 65.69, 66.97, 108.34, 108.94, 119.50, 120.26, 122.90, 122.94, 124.23, 133.01, 172.10, 174.54, 174.90, 176.68.

$^{1}$H NMR (500 MHz, pyridine-$d_5$): 0.91 (3H, t, J=8.0 Hz), 0.97 (3H, d, J=6.5 Hz), 1.10 (2H, m), 1.20 (2H, m), 1.30 (3H, m), 1.31 (3H, d, J=6.0 Hz), 1.35 (1H, m), 1.40 (2H, m), 1.45 (1H, m), 1.48 (1H, m), 1.50 (2H, m), 1.60 (2H, m), 1.84 (1H, m), 1.90 (1H, m), 2.05 (1H, brd, J=14.0), 2.31 (1H, m), 2.40 (1H, m), 3.25 (1H, dt, J=11.0, 2.0 Hz), 3.82 (1H, dd, J=14.5, 6.4 Hz), 3.91 (3H, s), 3.94 (1H, m), 4.20 (1H, dd, J=10.5, 14.5 Hz), 4.34 (1H, brd, J=13.5 Hz), 4.61 (1H, dt, J=10.5, 6.5 Hz), 4.76 (1H, brq, J=8.5 Hz), 5.16 (1H, t, J=10 Hz), 5.51 (1H, d, J=6.0 Hz), 5.65 (1H, d, J=5 Hz, OH), 7.16 (1H, t, J=7.5 Hz), 7.31 (1H, t, J=8.0 Hz), 7.34 (1H, d, J=10.0 Hz), 7.51 (1H, d, J=8.0 Hz), 7.55 (1H, s), 7.76 (1H, d, J=8.0 Hz), 8.27 (1H, d, J=10.5 Hz), 10.00 (1H, d, J=7.0 Hz).

HR-EIMS (m/z): 625.3774 (M$^+$, calcd for $C_{34}H_{51}N_5O_6$: 625.3839).

EXAMPLE 11

Preparation of Compound Ih by Hydrogenolysis of Compound Id

To a solution of compound Id (0.8 mg) in a 1 mL (1:1) mixture of methanol and ethyl acetate was added 10% palladium over charcoal (2 mg) and the mixture was evacuated to remove dissolved air. This mixture was flushed with hydrogen and this dagassing and flushing cycle was repeated three times. Finally the hydrogen was connected to the flask and the mixture was stirred for 2 hrs. The catalyst was removed by filtration through celite and the filtrate was evaporated under reduced pressure to give 0.7 mg of compound Ih as a colorless powder, $^1$H NMR (400 MHz, $CD_2Cl_2$): 0.86 (3H, d, J=6.5 Hz), 0.91 (3H, t, J=7.5 Hz), 1.03 (3H, t, J=7.0 Hz), 1.10–1.70 (8H, m), 1.78 (3H, m), 1.93 (1H, m), 1.96 (1H, m), 2.22 (1H, m), 2.32 (1H, m), 2.36 (2H, dt, J=7.5, 3.0 Hz), 2.42 (2H, q, J=7.0 Hz), 3.49 (1H, dd, J=10, 7.5 Hz), 3.53 (1H, dd, J=14, 7 Hz), 3.76 (1H, dd, J=14.5, 9.5 Hz), 3.81 (1H, dt, J=9.8, 4.5 Hz), 3.98 (1H, dt, J=10, 7 Hz), 4.14 (1H, ddd, J=10, 8.5, 6.5 Hz), 4.50 (1H, t, J=10.5 Hz), 4.72 (1H, dd, J=7.5, 1.5 Hz), 6.30 (1H, d, J=6 Hz, Trp-NH), 7.06 (1H, d, J=10.5 Hz), 7.10 (1H, dd, J=8, 1 Hz), 7.14 (1H, d, J=10.5 Hz), 7.16 (1H, dt, J=8, 0.5 Hz), 7.36 (1H, d, J=8.5 Hz), 7.58 (1H, d, J=8 Hz), 8.55 (1H, brs); ESI (m/z): 580 (M+H).

---

What is claimed is:

1. A compound having the formula:

(SEQ ID No.1)

wherein $R^1$ is $CH_3$ or $CH_2CH_3$;

$R^2$ is H or —$OCH_3$;

$R^3$ is H and $R^4$ is =O or (H, OH); or $R^3$ is OH and $R^4$ is =O or (H, H); and n is 0 or 1;

with the proviso that when n is 0, $R^1$ is $CH_2CH_3$, $R^3$ is H and $R^4$ is =O; and that when $R^1$ is $CH_3$, $R^3$ is H and $R^4$ is =O;

or a pharmaceutically acceptable salt thereof.

2. A compound of claim 1 where the stereochemical configuration is as follows:

(SEQ ID No. 1)

3. A compound of claim 2 wherein the substituents are as follows:

| Compound | n | $R^1$ | $R^2$ | $R^3$ | $R^4$ | SEQ. ID |
|---|---|---|---|---|---|---|
| Ia | 1 | Et | OMe | H | =O | No. 4 |
| Ib | 1 | Et | H | H | =O | No. 2 |
| Ic | 1 | Me | OMe | H | =O | No. 3 |
| Id | 0 | Et | OMe | H | =O | No. 5 |
| Ie | 1 | Et | OMe | H | (H,OH) | No. 4 |
| If | 1 | Et | OMe | OH | =O | No. 4 |
| Ig | 1 | Et | OMe | OH | (H,H) | No. 4 |
| Ih | 0 | Et | H | H | =O | No. 6 |

4. A pharmaceutical composition comprising an inert carrier and an effective amount of a compound of claim 1.

5. A pharmaceutical composition of claim 4 useful for the treatment of coccidiosis.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: circular ( i i ) MOLECULE TYPE: peptide ( x i ) SEQUENCE DESCRIPTION: SEQ ID NO:1:

Xaa  Xaa  Xaa  Xaa
    1

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: circular ( i i ) MOLECULE TYPE: peptide ( x i ) SEQUENCE DESCRIPTION: SEQ ID NO:2:

Trp  Xaa  Xaa  Ile
    1

( 2 ) INFORMATION FOR SEQ ID NO:3:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: circular ( i i ) MOLECULE TYPE: peptide ( x i ) SEQUENCE DESCRIPTION: SEQ ID NO:3:

Xaa  Xaa  Xaa  Val
    1

( 2 ) INFORMATION FOR SEQ ID NO:4:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: circular ( i i ) MOLECULE TYPE: peptide ( x i ) SEQUENCE DESCRIPTION: SEQ ID NO:4:

Xaa  Xaa  Xaa  Ile
    1

(2) INFORMATION FOR SEQ ID NO:5:

(i) SEQUENCE CHARACTERISTICS:
(A) LENGTH: 4 amino acids
(B) TYPE: amino acid
(C) STRANDEDNESS:
(D) TOPOLOGY: circular (ii) MOLECULE TYPE: peptide (xi) SEQUENCE DESCRIPTION: SEQ ID NO:5:

Xaa  Xaa  Pro  Ile
1

(2) INFORMATION FOR SEQ ID NO:6:

(i) SEQUENCE CHARACTERISTICS:
(A) LENGTH: 4 amino acids
(B) TYPE: amino acid
(C) STRANDEDNESS:
(D) TOPOLOGY: circular (ii) MOLECULE TYPE: peptide (xi) SEQUENCE DESCRIPTION: SEQ ID NO:6:

Trp  Xaa  Pro  Ile
1